Figure 1:
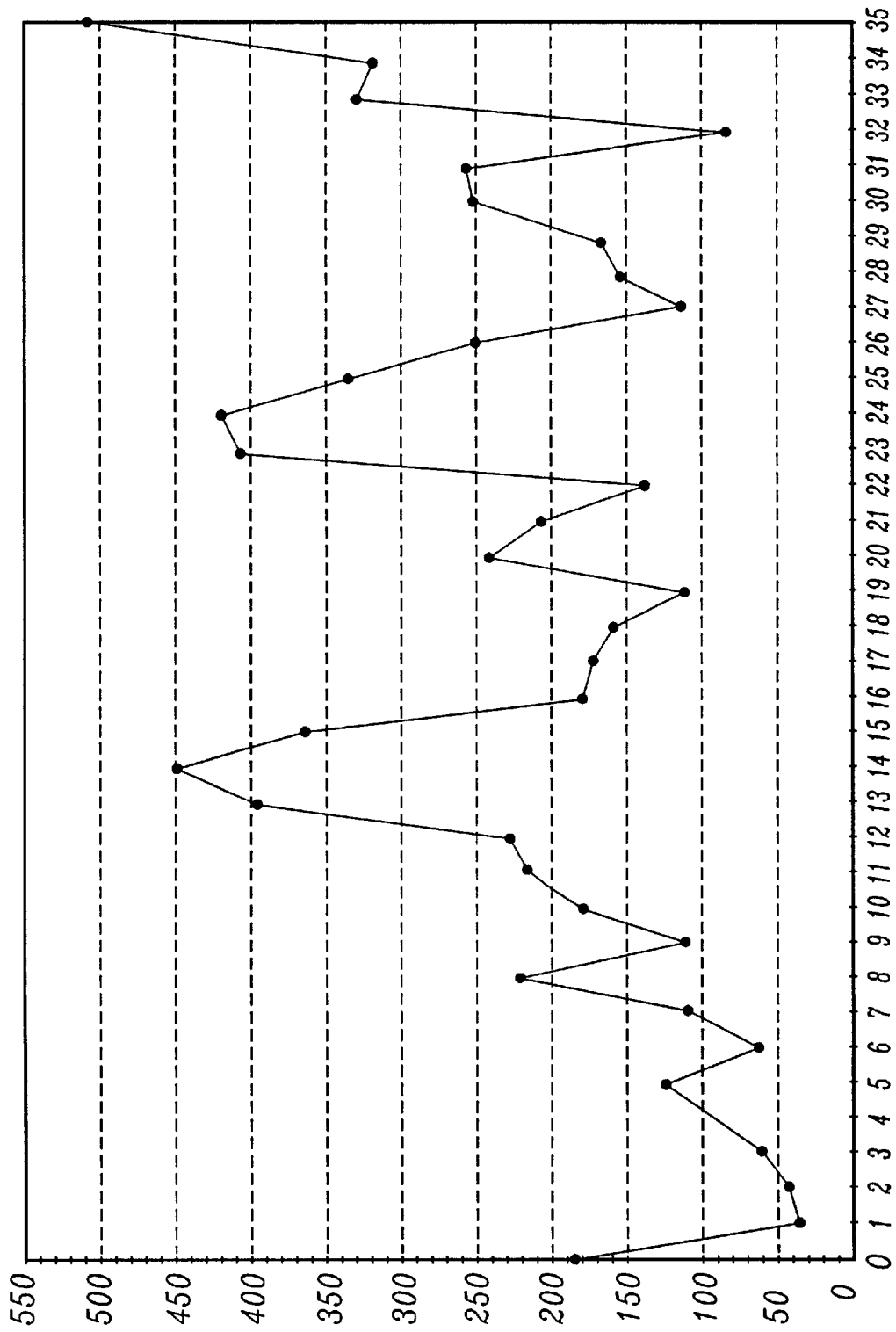

United States Patent [19]
Jeannin

[11] Patent Number: 5,858,387
[45] Date of Patent: Jan. 12, 1999

[54] N-PHENYLPYRAZOLE-BASED ANTIPARASITIC EXTERNAL DEVICE FOR CATTLE, IN PARTICULAR EAR-RINGS

[75] Inventor: Philippe Jeannin, Tournefeuille, France

[73] Assignee: Rhone Merieu, Lyons, France

[21] Appl. No.: 863,181

[22] Filed: May 27, 1997

Related U.S. Application Data

[63] Continuation-in-part of Ser. No. 692,112, Aug. 5, 1996, abandoned.

[30]    Foreign Application Priority Data

Mar. 29, 1996 [FR] France .................................. 96 04207
Mar. 26, 1997 [FR] France .................................. 97 03706

[51] Int. Cl.$^6$ .................................................. A01N 25/34
[52] U.S. Cl. .......................... 424/411; 424/405; 424/406; 514/341; 514/406
[58] Field of Search .................................. 424/402, 405, 424/406, 409, 411; 514/341, 406

[56]         References Cited

U.S. PATENT DOCUMENTS 5,556,873  9/1996  Huang et al. ........................... 514/407
5,620,696  4/1997  Kerwin .................................... 424/411

FOREIGN PATENT DOCUMENTS 0295117  12/1988  European Pat. Off. .

*Primary Examiner*—Neil S. Levy
*Attorney, Agent, or Firm*—Larson & Taylor

[57]         ABSTRACT

The external device such as a ring, in particular an ear-ring, intended to eliminate cattle parasites, in particular Haematobia irritans, formed of a matrix including from 0.1 to 40%, preferably from 2.5 to 10%, by weight, relative to the ear-ring, of an active substance which is at least one compound of formula (I) below:

this external device being designed to ensure efficacy for more than 30 weeks.

23 Claims, 2 Drawing Sheets

N-PHENYLPYRAZOLE-BASED ANTIPARASITIC EXTERNAL DEVICE FOR CATTLE, IN PARTICULAR EAR-RINGS

This application is a CIP of 08/692,112, filed Aug. 5,1996, now abandoned.

The present invention relates to external antiparasitic devices for cattle, in particular in the form of a ring and more particularly an ear-ring.

The invention also relates to the use of active compounds for the manufacture of such external devices, as well as to a treatment process relating thereto.

One of the main cattle parasites is a fly known as *Haematobia irritans* (horn fly), the adult of which is a permanent haematophagic parasite of cattle. This parasite, which is encountered especially in North America, but also in Europe, Australia and Southern Africa, can lead to considerable economic losses, as regards both weight gain and milk production, in particular when the parasite density exceed 50 flies per animal, while, in certain regions, it is not uncommon to exceed 200 flies per animal.

At the present time, it is not known how to control this parasite effectively. The difficulty in controlling it results mainly from the fact that the parasite density is constant, since this is a parasite which possesses wings in its adult form, and can thus pass from one herd to another and thereby permanently reinfest herds for which a procedure to control this parasite has been implemented. In addition, in certain regions, the parasite density lasts throughout the year. Breeders currently have few effective means of control available to them, in particular in the case of rearing in open grazing, even by ensuring constant control of these parasites, that is to say regular and closely-timed supplies of insecticides, all the more so since flies have developed resistance to pyrethroids and to organophosphorus compounds.

Ear-rings intended, as their name implies, to be attached to the animal's ear and to release an active substance over a longer or shorter period have also been proposed. These rings consist of a matrix, usually a plastic matrix, which incorporates the active substance and is able to release it over time. The aim of these rings is thus, theoretically, to ensure long-lasting protection.

However, despite the activity claims, in the field rings do not display the efficacy required to ensure that these parasites are actually eliminated. The reason for this may be the low activity of the active substance included in the matrix. Another reason may be the accelerated degradation of these active substances under the effect of climatic factors, such as light, heat and rain. Lastly, the control of the release of the active substance from the matrix is widely overevaluated. The release generally proves to be difficult and variable, and it may depend highly on the manufacturing conditions, which may vary from one batch to another, and on the conditions of use, in particular climatic variations, and especially humidity and temperature, etc. In addition, only a relatively small amount of the active substance incorporated is actually released and it proves to be difficult to be able to control and optimize its release.

Only organophosphorus compounds have made it possible to obtain a release over about 4 months, but by means of considerable concentrations of active substance, of about 40% by weight.

Patent applications WO-A-87/03781, EP-A-0,295,117, EP-A-0,296,381 and EP-A-0,500,209 relate to a family of insecticides which are N-phenylpyrazoles. These substances are described as being active against a very large number of parasites encountered in various fields, namely agriculture, public health and human and veterinary medicine.

EP-A-0,500,209 indicates that, in the field of public health, these compounds may be used to combat a large number of insects, in particular flies and among which are mentioned "hornfly" or *Haematobia irritans*. However, *Haematobia irritans* is not mentioned in the context of treating the animals.

These substances may be applied in different ways, namely via the oral, parenteral, percutaneous or topical route. Topical administration itself covers various possibilities, namely sprays, powders, baths, showers, jets, greases, shampoos, creams, waxes, preparations of skin solution type (pour-on) and external devices such as ear-rings and collars to provide local or systemic treatment.

EP-A-0,295,117 and EP-A-0,500,209 also propose a composition for slow release which may be in the form of a collar or ear-rings, to control harmful insects. Such a formulation may comprise from 0.5 to 25% active material, from 75 to 99.5% polyvinyl chloride and a catalytic amount of a plasticizer, dioctyl phthalate.

U.S. Pat. No. 5,472,955 illustrates the difficult nature of controlling *Haematobia irritans* and indicates that it is necessary to make use of a combination of two active compounds, diazinon and chlorpyrifos, in high concentration in a slow-release device. That document indicates that the compounds taken alone are not as effective as the synergistic combination of the two compounds. Diazinon simply affords an acceptable level of control of *Haemotobia irritans* over 3 to 5 months, whereas chlor-pyrifos appears to be incapable of this. The said document specifies at the end that an ear-ring containing a 40% mixture was much more active than two ear-rings applied on the same animal and containing 21.4% diazinon as sole active ingredient. Although the proportion of active principle may range in theory from 8 to 40%, it is preferably between 20 and 40%. In the case of ear-rings, the proportion is from 10 to 50% by weight, preferably from 30 to 45% and optimally 40% by weight.

None of the documents cited either describes or suggests that it is possible to effectively protect cattle against *Haemotobia irritans*, over a long period, using ear-rings comprising a single active compound, for which, in addition, a specialist might expect to encounter conventional problems of release from the rings and thus problems of activity.

As with the other insecticides of the prior art, these N-phenylpyrazoles are, indeed, subject to the same difficulties in the context of external release devices such as ear-rings.

It therefore did not appear to be conceivable to be able thus to effectively control parasites liable to be found on any part of the animal, which is all the more the case for winged parasites which give rise to a parasite density as high and constant as that of *Haemotobia irritans*.

The Applicant has now found, entirely surprisingly, that it is actually possible to effectively eliminate *Haemotobia irritans* from cattle by using an ear-ring using an N-phenylpyrazole under specific concentration conditions. The Applicant has observed with surprise that, despite the problems associated with release by ear-rings, the efficacy extended throughout the animal's body and was very long-lasting and that, for example, with rings loaded to a content of 10%, it was possible to exceed 32 weeks at an efficacy of greater than 90%.

The active substance acts by simple contact, the parasite becoming impregnated with it on contact with the hairs and the skin.

The subject of the present invention is thus an external device such as a ring, in particular an ear-ring, intended to eliminate cattle parasites, in particular *Haemotobia irritans*, this device being formed of a matrix including from 0.1 to 40% by weight, relative to the device, of an active substance which is at least one compound of formula (I) below:

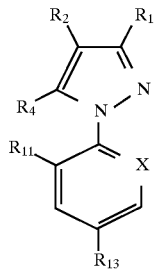

in which:
- $R_1$ is CN or methyl or a halogen atom;
- $R_2$ is $S(O)_nR_3$ or 4,5-dicyanoimidazol-2-yl or haloalkyl;
- $R_3$ is alkyl or haloalkyl;
- $R_4$ represents a hydrogen or halogen atom; or a radical $NR_5R_6$, $S(O)_mR_7$, $C(O)R_7$, $C(O)O-R_7$, alkyl, haloalkyl or $OR_8$ or a radical $-N=C(R_9)(R_{10})$;
- $R_5$ and $R_6$ independently represent a hydrogen atom or an alkyl, haloalkyl, C(O)alkyl, alkoxycarbonyl or $S(O)_rCF_3$ radical; or $R_5$ and R6 may together form a divalent alkylene radical which may be interrupted by one or two divalent hetero atoms, such as oxygen or sulphur;
- $R_7$ represents an alkyl or haloalkyl radical;
- $R_8$ represents an alkyl or haloalkyl radical or a hydrogen atom;
- $R_9$ represents an alkyl radical or a hydrogen atom;
- $R_{10}$ represents a phenyl or heteroaryl group optionally substituted with one or more halogen atoms or groups such as OH, -O-alkyl, -S-alkyl, cyano or alkyl;
- $R_{11}$, and $R_{12}$ represent, independently of each other, a hydrogen or halogen atom, or optionally CN or $NO_2$;
- $R_{13}$ represents a halogen atom or a haloalkyl, haloalkoxy, $S(O)_qCF_3$ or $SF_5$ group;
- m, n, q and r represent, independently of each other, an integer equal to 0, 1 or 2;
- X represents a trivalent nitrogen atom or a radical $C-R_{12}$, the other three valency positions of the carbon atom forming part of the aromatic ring;
- with the proviso that when $R_1$ is methyl, either $R_3$ is haloalkyl, $R_4$ is $NH_2$, $R_{11}$ is Cl, $R_{13}$ is $CF_3$ and X is N; or $R_2$ is 4,5-dicyanoimidazol-2-yl, $R_4$ is Cl, $R_{11}$ is Cl, $R_{13}$ is $CF_3$ and X is $=C-Cl$, this external device being designed to ensure efficacy for more than 30 weeks.

Preferably, the compound of formula (I) is such that:
- $R_1$ is CN or methyl;
- $R_2$ is $S(O)_nR_3$;
- $R_3$ is alkyl or haloalkyl;
- $R_4$ represents a hydrogen or halogen atom; or a radical $NR_5R_6$, $S(O)_mR_7$, $C(O)R_7$, alkyl, haloalkyl or $OR_8$ or a radical $-N=C(R_9)(R_{10})$;
- $R_5$ and $R_6$ independently represent a hydrogen atom or an alkyl, haloalkyl, C(O)alkyl or $S(O)_rCF_3$ radical; or $R_5$ and $R_6$ may together form a divalent alkylene radical which may be interrupted by one or two divalent hetero atoms, such as oxygen or sulphur;
- $R_7$ represents an alkyl or haloalkyl radical;
- $R_8$ represents an alkyl or haloalkyl radical or a hydrogen atom;
- $R_9$ represents an alkyl radical or a hydrogen atom;
- $R_{10}$ represents a phenyl or heteroaryl group optionally substituted with one or more halogen atoms or groups such as OH, -O-alkyl, -S-alkyl, cyano or alkyl;
- $R_{11}$ and $R_{12}$ represent, independently of each other, a hydrogen or halogen atom;
- $R_{13}$ represents a halogen atom or a haloalkyl, haloalkoxy, $S(O)_qCF_3$ or $SF_5$ group;
- m, n, q and r represent, independently of each other, an integer equal to 0, 1 or 2;
- X represents a trivalent nitrogen atom or a radical $C-R_{12}$, the other three valency positions of the carbon atom forming part of the aromatic ring;
- with the proviso that when $R_1$ is methyl, then $R_3$ is haloalkyl, $R_4$ is $NH_2$, $R_{11}$ is Cl, $R_{13}$ is $CF_3$ and X is N.

The compounds of formula (I) in which $R_1$ is CN will be selected most particularly. The compounds in which $R_2$ is $S(O)_nR_3$, preferably with n=1, $R_3$ preferably being $CF_3$ or alkyl, for example methyl or ethyl, or alternatively n=0, $R_3$ preferably being $CF_3$, as well as those in which $X=C-R_{12}$, $R_{12}$ being a halogen atom, will also be selected. The compounds in which $R_{11}$ is a halogen atom and those in which $R_{13}$ is haloalkyl, preferably $CF_3$, are also preferred. In the context of the present invention, the compounds which combine two or more of these characteristics will advantageously be selected.

A preferred class of compounds of formula (I) consists of compounds such that $R_1$ is CN, $R_3$ is haloalkyl, preferably $CF_3$, or ethyl, $R_4$ is $NH_2$, $R_{11}$ and $R_{12}$ are, independently of each other, a halogen atom, and/or $R_{13}$ is haloalkyl.

In the invention, the alkyl radicals may contain generally from 1 to 6 carbon atoms. The cycle formed between the divalent alkylene radical representing $R_5$ and $R_6$, as well as with the nitrogen atom to which $R_5$ and $R_6$ are linked may be generally a cycle of 5, 6 or 7 links.

A compound of formula (I) which is most particularly preferred in the invention is 1-[2,6-$Cl_2$4-$CF_3$phenyl]3-CN4-[SO-$CF_3$]5-$NH_2$pyrazole, referred to hereinbelow as compound A.

Mention may also be made of two compounds which differ from the above A by the following characteristics:
1 - n=0, $R_3$=$CF_3$
2 - n=1, $R_3$ =ethyl.

Compounds of formula (I) may be prepared according to one or other of the processes described in patent applications WO-A-87/3781, 93/6089, 94/21606 or European patent application EP-A-0,295,117, or any other process falling within the competence of a specialist skilled in the art of chemical synthesis. For the chemical preparation of the products of the invention, a person skilled in the art is considered as having at his disposal, inter alia, all the contents of "Chemical Abstracts" and the documents which are cited therein.

However, low concentrations of from 1 to 15% by weight and more particularly, especially for compound A, from 2.5 to 10% are preferred. Under optimum conditions, the rings according to the invention comprise from 5 to 10% by weight of active substance, in particular of compound A.

Within the context of the present invention, the external devices obviously include any device intended to be attached to the animal's body and which allows the active substance to be released under the efficacy conditions of the invention.

By acting on the concentration of active substance and/or on the composition, ear-rings can be made with an efficacy towards *Haemotobia irritans* which can exceed 90% and even 95% for more than 30 weeks, in particular for 32 weeks.

It is noteworthy that this total and very long-lasting efficacy is obtained by the compound according to the invention alone, without addition of another insecticide.

The active substance can however comprise, in addition to the compound of formula (I), another insecticide, for example pyrethroids (in particular permethrin, cypermethrin, etc.), organophosphorus compounds (for example diazinon), imidacloprid and IGRs (insect growth regulators).

These active substances may be combined in different ways. The active substances are either combined within the same ear-ring, including a composite ear-ring, namely one made of two parts, each part including one of the active substances, or use may be made of two separate ear-rings, each comprising one of the active substances and each preferably intended to be placed on a different ear of the animal. In the latter case, the subject of the invention is a kit comprising these two ear-rings.

The matrix of the external devices according to the invention may be based on polyvinyl chloride (PVC) (see U.S. Pat. Nos. 3,318,769, 3,852,416, 4,150,109, 5,437,869) and other vinyl polymers, to which additives such as plasticizers, pigments, etc. are optionally added. In general, the matrices usually used in the common external devices of ear-ring and collar type can be used.

The plasticizers may be chosen in particular from adipates, phthalates, phosphates and citrates.

One or more plasticizers will preferably be added to the PVC, these plasticizers being chosen, in particular, from the following compounds:

diethyl phthalate
dioctyl sebacate
dioctyl adipate
diisodecyl phthalate
acetyl tributyl citrate
diethyl hexyl phthalate
di-n-butyl phthalate
benzyl butyl phthalate
acetyl tributyl citrate
tricresyl phosphate
2-ethylhexyl diphenyl phosphate.

Even more peferably, a PVC matrix will be used in the presence of a first remanent plasticizer as described above and of a second plasticizer, in particular according to EP-A-0,539,295 and EP-A-0,537,998.

Among the secondary plasticizers, mention may be made of the following products:

acetyl triethyl citrate
triethyl citrate
triacetin
diethylene glycol monoethyl ether
triphenyl phosphate.

A common stabilizer may also be added thereto.

Another subject of the present invention is a process for the elimination of external parasites, in particular *Haemotobia irritans*, from cattle, in particular cattle reared in the open air and more particularly in open grazing, which consists in attaching to the animal the ear-ring or -rings according to the present invention, which ensure(s) the effective and long-lasting protection described above.

This process generally consists in attaching to the animal 1 or 2 ear-rings or the like loaded with compound according to the invention, preferably with compound A. These rings have the specifications mentioned above.

The process may also comprise the combined use of other insecticides, by the use of rings, composite rings or separate rings as described above.

In general, the process according to the invention envisages the animal wearing the ring or rings throughout the year.

The aim of the method is non-therapeutic and is in particular to cleanse the animals' skin and hairs by eliminating the parasites which are present thereon, as well as their residues and dejections. The result of this is that the animals are no longer stressed by the parasites and their bites, this having positive consequences, for example on their growth and on the use of their food ration.

Another subject of the invention is a therapeutic method using the external device according to the invention, intended for treating and preventing parasitoses having pathogenic consequences.

The subject of the present invention is also the use of a compound corresponding to formula (I) above, for the preparation of external devices such as rings, in particular ear-rings, intended to be attached to cattle in order to ensure elimination of *Haemotobia irritans* to a high degree of efficacy and over a period exceeding 30 weeks. The devices as above are concerned. The use according to the invention preferably includes the incorporation of 0.1 to 40% by weight, preferably from 1 to 15% by weight, of the compound of formula (I) in a matrix intended to form the external device. Even more preferably, the incorporation is made in a proportion of 2.5 to 10% by weight, and even from 5 to 10%.

Preferably, the use according to the invention is directed towards the manufacture of ear-rings.

Preferably, the use according to the invention is directed towards the production of external devices or ear-rings having an efficacy of greater than 90% or 95%.

Figure 2:
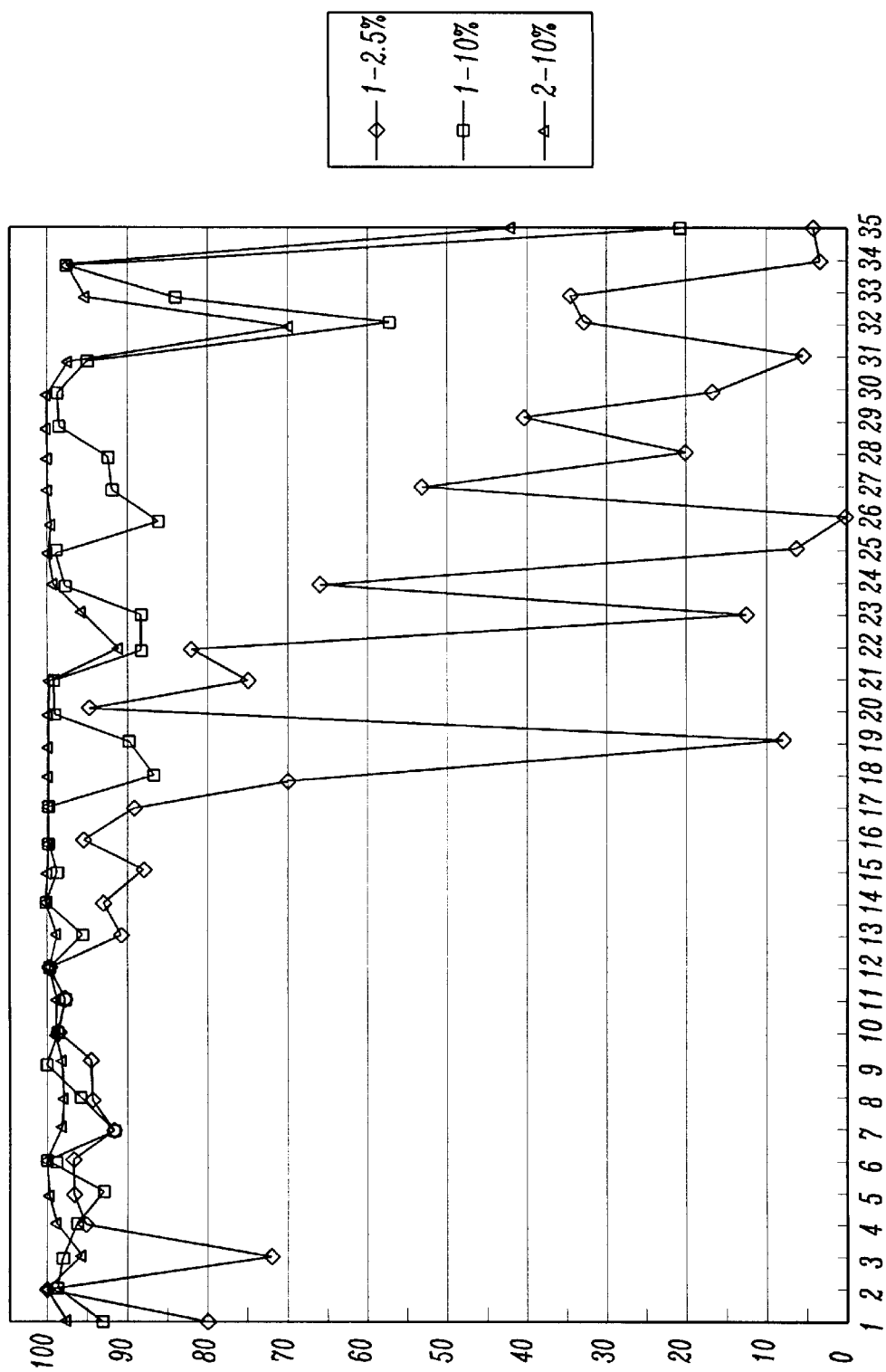

The present invention will now be described in greater detail by means of a non-limiting embodiment example which refers to the drawing in which:

FIG. 1 is a graph showing the population of *Haemotobia irritans* in a control group, with the time (weeks) on the X-axis and the arithmetic mean on the Y-axis; and FIG. 2 is a graph with the time (weeks) on the X-axis and the arithmetic mean of the *Haematobia irritans* count on the Y-axis.

The following groups were prepared:

Group A: controls: 10 heifers
Group B: 10 heifers which have received ear-rings containing 2.5% compound A. Each animal receives one ring.
Group C: 10 heifers which have received ear-rings containing 10% compound A. Each animal receives one ring.
Group D: 10 heifers which have received ear-rings containing 10% compound A. Each animal receives two ring, one per ear.

The ear-rings are made based on polyvinyl chloride (PVC), to which a stabilizer (Mark 152S), a plasticizer (acetyl tributyl citrate) and a pigment (titanium dioxide) are added. They are manufactured by injection-molding.

Each group of animals is placed in a pasture of about 100 to 150 acres (40 to 60 hectares).

The infestation with *Haemotobia irritans* is of natural origin.

The chronology of events is as follows:
the ear-rings are inserted on day 0. The *Haemotobia irritans* parasites are then counted every 6, 7 or 8 days.

An efficacy of greater than 90% and even greater than 95%, which can be up to 100%, over long periods was obtained with all of the formulations according to the invention. The 2.5% composition proved to be greater than 90% effective for 18 weeks. When inserted in only one ear or in both ears, the 10% composition also affords greater than 90% protection, over a much longer period of up to 32 weeks. The use of two ear-rings per animal affords greater protection, which is close to 100% over the entire 32-week period.

The results are reported in FIGS. 1 and 2.

I claim:

1. Process for the elimination of *Haematobia irritans* from cattle, in which one attaches to the cattle an external device formed of a matrix including from 1 to 15% by weight, relative to the device, of an active substance which is at least one compound of formula (I) below:

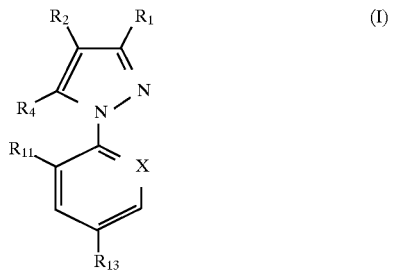

in which:
$R_1$ is CN or methyl or a halogen atom;
$R_2$ is $S(O)_n R_3$ or 4,5-dicyanoimidazol-2-yl or haloalkyl;
$R_3$ is alkyl or haloalkyl;
$R_4$ represents a hydrogen or halogen atom; or a radical $NR_5 R_6$, $S(O)_m R_7$, $C(O)R_7$, $C(O)O—R_7$, alkyl, haloalkyl or $OR_8$ or a radical $—N=C(R_9)(R_{10})$;
$R_5$ and $R_6$ independently represent a hydrogen atom or an alkyl, haloalkyl, C(O)alkyl, alkoxycarbonyl or $S(O)_r CF_3$ radical; or $R_5$ and $R_6$ may together form a divalent alkylene radical which may be interrupted by one or two divalent hetero atoms;
$R_7$ represents an alkyl or haloalkyl radical;
$R_8$ represents an alkyl or haloalkyl radical or a hydrogen atom;
$R_9$ represents an alkyl radical or a hydrogen atom;
$R_{10}$ represents a phenyl or heteroaryl group optionally substituted with one or more halogen atoms or groups such as OH, —O-alkyl, —S-alkyl, cyano or alkyl;
$R_{11}$ and $R_{12}$ represent, independently of each other, a hydrogen or halogen atom or optionally CN or $N_{O2}$;
$R_{13}$ represents a halogen atom or a haloalkyl, haloalkoxy, $S(O)_q CF_3$ or $SF_5$ group;
m, n, q and r represent, independently of each other, an integer equal to 0, 1 or 2;
X represents a trivalent nitrogen atom or a radical $C—R_{12}$, the other three valency positions of the carbon atom forming part of the aromatic ring;
with the proviso that when $R_1$ is methyl, either $R_3$ is haloalkyl, $R_4$ is $NH_2$, $R_{11}$ is Cl, $R_{13}$ is $CF_3$ and X is N, or $R_2$ is 4,5-dicyanoimidazol-2-yl, $R_4$ is Cl, $R_{11}$ is Cl, $R_{13}$ is $CF_3$ and X is =C—Cl;
in order to ensure the elimination of *Haemotobia irritans* over a period exceeding 30 weeks.

2. Process according to claim 1, wherein the compound of formula (I) is such that:
$R_1$ is CN or methyl;
$R_2$ is $S(O)_n R_3$;
$R_3$ is alkyl or haloalkyl;
$R_4$ represents a hydrogen or halogen atom; or a radical $NR_5 R_6$, $S(O)_m R_7$, $C(O)R_7$, alkyl, haloalkyl or $OR_8$ or a radical $—N=C(R_9)(R_{10})$;
$R_5$ and $R_6$ independently represent a hydrogen atom or an alkyl, haloalkyl, C(O)alkyl or $S(O)_r CF_3$ radical; or $R_5$ and $R_6$ may together form a divalent alkylene radical which may be interrupted by one or two divalent hetero atoms;
$R_7$ represents an alkyl or haloalkyl radical;
$R_8$ represents an alkyl or haloalkyl radical or a hydrogen atom;
$R_9$ represents an alkyl radical or a hydrogen atom;
$R_{10}$ represents a phenyl or heteroaryl group optionally substituted with one or more halogen atoms or groups selected from OH, —O-alkyl, —S-alkyl, cyano or alkyl;
$R_{11}$ and $R_{12}$ represent, independently of each other, a hydrogen or halogen atom;
$R_{13}$ represents a halogen atom or a haloalkyl, haloalkoxy, $S(O)_q CF_3$ or $SF_5$ group;
m, n, q and r represent, independently of each other, an integer equal to 0, 1 or 2;
X represents a trivalent nitrogen atom or a radical $C—R_{12}$ the other three valency positions of the carbon atom forming part of the aromatic ring;
with the proviso that when $R_1$ is methyl, then $R_3$ is haloalkyl, $R_4$ is $NH_2$, $R_{11}$ is Cl, $R_{13}$ is $CF_3$ and X is N.

3. Process according to claim 2, wherein the compound of formula (I) is such that $R_1$ is CN.

4. Process according to claim 2, wherein the compound of formula (I) is such that $R_{13}$ is a haloalkyl.

5. Process according to claim 2, wherein the compound of formula (I) is such that $R_{13}$ is $CF_3$.

6. Process according to claim 2, wherein the compound of formula (I) is such that $R_2$ is $S(O)_n R_3$.

7. Process according to claim 6, wherein n=1 and $R_3$ is chosen among the group consisting of $CF_3$ methyl, ethyl.

8. Process according to claim 6, wherein n=0 and $R_3$ is $CF_3$.

9. Process according to claim 2, wherein the compound of formula (I) is such that X is $C—R_{12}$ with $R_{12}$ being a halogen atom.

10. Process according to claim 2, wherein the compound of formula (I) is such that $R_1$ is CN, $R_3$ is haloalkyl, $R_4$ is $NH_2$, $R_{11}$ and $R_{12}$ are, independently of each other, a halogen atom, and/or $R_{13}$ is haloalkyl.

11. Process according to claim 2, wherein the compound of formula (I) is chosen among the group consisting of 5-amino-3-cyano-1-(2,6-dichloro-4-trifluoromethylphenyl)-4trifluoromethylsulfinylpyrazole. and its derivatives with n=0 and $R_3$ is $CF_3$, and n=1 and $R_3$ is ethyl.

12. Process according to claim 2, wherein the compound of formula (I) is incorporated in a concentration of 1 to 15% by weight.

13. Process according to claim 2, wherein the compound of formula (I) is present in a concentration of from 2.5 to 10% by weight.

14. Process according to claim 2, wherein the compound of formula (I) is present in a concentration of from 5 to 10% by weight.

15. Process according to claim 11, wherein the compound of formula (I) is incorporated in a concentration of 1 to 15% by weight.

16. Process according to claim 11, wherein the compound of formula (I) is present in a concentration of from 2.5 to 10% by weight.

17. Process according to claim 11, wherein the compound of formula (I) is present in a concentration of from 5 to 10% by weight.

18. Process according to claim 2, wherein the external device is an ear-ring.

19. Process according to claim 11, wherein the efficacy is greater than 90% over a long period of time exceeding 30 weeks.

20. Process according to claim 2, wherein one attaches to the cattle another external device comprising an insecticide different than the compound of formula (I).

21. Process according to claim 20, wherein the insecticide is chosen among the group consisting of: pyrethroids, permethrin, cypermethrin, organophosphorous compounds, diazinon, imidacloprid and insect growth regulators.

22. Process according to claim 2, wherein the external device attached to the cattle comprises the compound of formula (I) and an insecticide different than the compound of formula (I).

23. Process according to claim 22, wherein the insecticide is chosen among the group consisting of: pyrethroids, permethrin, cypermethrin, organophosphorous compounds, diazinon, imidacloprid and insect growth regulators.

* * * * *